United States Patent
Shelton, IV et al.

(10) Patent No.: US 7,407,078 B2
(45) Date of Patent: Aug. 5, 2008

(54) SURGICAL STAPLING INSTRUMENT HAVING FORCE CONTROLLED SPACING END EFFECTOR

(75) Inventors: Frederick E. Shelton, IV, Hillsboro, OH (US); Jerome R. Morgan, Cincinnati, OH (US)

(73) Assignee: Ehthicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/231,456

(22) Filed: Sep. 21, 2005

(65) Prior Publication Data

US 2007/0075114 A1    Apr. 5, 2007

(51) Int. Cl.
*A61B 17/072* (2006.01)
(52) U.S. Cl. .................. 227/180.1; 227/19; 227/178.1; 227/181.1
(58) Field of Classification Search .............. 227/178.1, 227/19, 175.1; 606/8, 153, 144; 411/21, 411/24
See application file for complete search history.

(56) References Cited

U.S. PATENT DOCUMENTS

| | | |
|---|---|---|
| 2,037,727 A | 4/1936 | Chapelle |
| 3,269,630 A | 8/1966 | Fleischer |
| 3,734,207 A | 5/1973 | Fishbein |
| 3,894,174 A | 7/1975 | Cartum |
| 3,940,844 A | 3/1976 | Colby et al. |
| 4,415,112 A | 11/1983 | Green |
| 4,475,679 A | 10/1984 | Fleury, Jr. |
| 4,520,817 A | 6/1985 | Green |
| 4,526,174 A | 7/1985 | Froehlich |
| 4,605,001 A | 8/1986 | Rothfuss et al. |
| 4,606,343 A | 8/1986 | Conta et al. |
| 4,608,981 A | 9/1986 | Rothfuss et al. |
| 4,709,120 A | 11/1987 | Pearson |
| 4,869,415 A | 9/1989 | Fox |
| 4,892,244 A | 1/1990 | Fox et al. |
| 4,941,623 A | 7/1990 | Pruitt |
| 4,955,959 A | 9/1990 | Tompkins et al. |
| 5,027,834 A | 7/1991 | Pruitt |

(Continued)

FOREIGN PATENT DOCUMENTS

DE    69328576    1/2001

(Continued)

OTHER PUBLICATIONS

EPO Search Report, U.S. Appl. No. 06254867.2, May 1, 2007, pp. 1-8.

*Primary Examiner*—Brian D. Nash
(74) *Attorney, Agent, or Firm*—Frost Brown Todd LLC

(57) ABSTRACT

A surgical instrument for being endoscopically or laparoscopically inserted into a surgical site for simultaneous stapling and severing of tissue includes force adjusted spacing between an upper jaw (anvil) and a lower jaw (staple cartridge engaged to an elongate staple channel) so that the height of staple formation corresponds to the thickness of the tissue, yet does not exceed the height range that may be accommodated by the length of the staples. In particular, resilient structures are formed into an E-beam firing bar that includes a cutting surface (knife) that severs tissue between a top pin that engages the anvil and a middle pin and lower foot that engage the lower jaw. The resilience responds to the force exerted by clamped tissue to vary the spacing.

17 Claims, 8 Drawing Sheets

U.S. PATENT DOCUMENTS

| | | | |
|---|---|---|---|
| 5,031,814 A | 7/1991 | Tompkins et al. | |
| 5,040,715 A | 8/1991 | Green et al. | |
| 5,065,929 A | 11/1991 | Schulze et al. | |
| 5,080,556 A | 1/1992 | Carreno | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,156,315 A | 10/1992 | Green et al. | |
| 5,200,280 A | 4/1993 | Karasa | |
| 5,207,697 A | 5/1993 | Carusillo et al. | |
| 5,211,649 A | 5/1993 | Kohler et al. | |
| 5,246,156 A | 9/1993 | Rothfuss et al. | |
| 5,253,793 A | 10/1993 | Green et al. | |
| RE34,519 E | 1/1994 | Fox et al. | |
| 5,275,323 A | 1/1994 | Schulze et al. | |
| 5,307,976 A * | 5/1994 | Olson et al. | 227/175.3 |
| 5,309,927 A | 5/1994 | Welch | |
| 5,318,221 A | 6/1994 | Green et al. | |
| 5,332,142 A | 7/1994 | Robinson et al. | |
| 5,350,400 A | 9/1994 | Esposito et al. | |
| 5,379,933 A | 1/1995 | Green et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,397,046 A | 3/1995 | Savage et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,432,322 A | 7/1995 | Green et al. | |
| 5,433,721 A | 7/1995 | Hooven et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A * | 11/1995 | Knodel et al. | 227/176.1 |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,482,197 A | 1/1996 | Green et al. | |
| 5,484,095 A * | 1/1996 | Green et al. | 227/181.1 |
| 5,485,947 A * | 1/1996 | Olson et al. | 227/176.1 |
| 5,485,952 A | 1/1996 | Fontayne | |
| 5,487,499 A | 1/1996 | Sorrentino et al. | |
| 5,487,500 A | 1/1996 | Knodel et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,937 A * | 7/1996 | Boiarski et al. | 227/175.3 |
| 5,549,628 A | 8/1996 | Cooper et al. | |
| 5,553,675 A | 9/1996 | Pitzen et al. | |
| 5,554,169 A | 9/1996 | Green et al. | |
| 5,562,239 A | 10/1996 | Boiarski et al. | |
| 5,562,241 A | 10/1996 | Knodel et al. | |
| 5,574,431 A | 11/1996 | McKeown et al. | |
| 5,575,803 A | 11/1996 | Cooper et al. | |
| 5,582,611 A | 12/1996 | Tsuruta et al. | |
| 5,584,425 A | 12/1996 | Savage et al. | |
| 5,586,711 A | 12/1996 | Plyley et al. | |
| 5,628,446 A | 5/1997 | Geiste et al. | |
| 5,632,432 A | 5/1997 | Schulze et al. | |
| 5,636,779 A | 6/1997 | Palmer | |
| 5,651,491 A | 7/1997 | Heaton et al. | |
| 5,653,374 A | 8/1997 | Young et al. | |
| 5,662,258 A | 9/1997 | Knodel et al. | |
| 5,667,517 A | 9/1997 | Hooven | |
| 5,673,840 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,688,270 A | 11/1997 | Yates et al. | |
| 5,692,668 A * | 12/1997 | Schulze et al. | 227/175.1 |
| 5,693,042 A | 12/1997 | Boiarski et al. | |
| 5,702,408 A | 12/1997 | Wales et al. | |
| 5,704,534 A | 1/1998 | Huitema et al. | |
| 5,706,998 A | 1/1998 | Plyley et al. | |
| 5,709,680 A | 1/1998 | Yates et al. | |
| 5,713,505 A | 2/1998 | Huitema | |
| 5,715,988 A | 2/1998 | Palmer | |
| 5,718,359 A | 2/1998 | Palmer et al. | |
| 5,735,445 A | 4/1998 | Vidal et al. | |
| 5,747,953 A | 5/1998 | Philipp | |
| 5,752,644 A | 5/1998 | Bolanos et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,782,397 A | 7/1998 | Koukline | |
| 5,796,188 A | 8/1998 | Bays | |
| 5,797,537 A | 8/1998 | Oberlin et al. | |
| 5,797,538 A | 8/1998 | Heaton et al. | |
| 5,807,393 A | 9/1998 | Williamson, IV et al. | |
| 5,817,093 A | 10/1998 | Williamson, IV et al. | |
| 5,823,066 A | 10/1998 | Huitema et al. | |
| 5,826,776 A | 10/1998 | Schulze et al. | |
| 5,833,690 A | 11/1998 | Yates et al. | |
| 5,843,132 A | 12/1998 | Ilvento | |
| 5,865,361 A | 2/1999 | Milliman et al. | |
| 5,878,938 A | 3/1999 | Bittner et al. | |
| 5,893,506 A | 4/1999 | Powell | |
| 5,894,979 A | 4/1999 | Powell | |
| 5,911,353 A | 6/1999 | Bolanos et al. | |
| 5,918,791 A | 7/1999 | Sorrentino et al. | |
| 5,954,259 A | 9/1999 | Viola et al. | |
| 5,988,479 A | 11/1999 | Palmer | |
| 6,010,054 A * | 1/2000 | Johnson et al. | 227/176.1 |
| 6,017,356 A | 1/2000 | Frederick et al. | |
| 6,022,352 A | 2/2000 | Vandewalle | |
| 6,024,741 A | 2/2000 | Williamson, IV et al. | |
| 6,024,748 A | 2/2000 | Manzo et al. | |
| 6,032,849 A * | 3/2000 | Mastri et al. | 227/176.1 |
| 6,079,606 A * | 6/2000 | Milliman et al. | 227/175.2 |
| 6,083,234 A | 7/2000 | Nicholas et al. | |
| 6,109,500 A * | 8/2000 | Alli et al. | 227/175.2 |
| H1904 H | 10/2000 | Yates et al. | |
| 6,126,670 A | 10/2000 | Walker et al. | |
| 6,131,789 A | 10/2000 | Schulze et al. | |
| 6,155,473 A | 12/2000 | Tompkins et al. | |
| 6,156,056 A | 12/2000 | Kearns et al. | |
| 6,202,914 B1 | 3/2001 | Geiste et al. | |
| 6,223,835 B1 | 5/2001 | Habedank et al. | |
| 6,241,139 B1 | 6/2001 | Milliman et al. | |
| 6,250,532 B1 | 6/2001 | Greenet et al. | |
| 6,264,087 B1 | 7/2001 | Whitman | |
| 6,273,897 B1 | 8/2001 | Dalessandro et al. | |
| 6,315,184 B1 | 11/2001 | Whitman | |
| 6,320,123 B1 | 11/2001 | Reimers | |
| 6,325,810 B1 | 12/2001 | Hamilton et al. | |
| 6,330,965 B1 | 12/2001 | Milliman et al. | |
| 6,358,224 B1 | 3/2002 | Tims et al. | |
| 6,416,486 B1 | 7/2002 | Wampler | |
| 6,443,973 B1 | 9/2002 | Whitman | |
| 6,488,197 B1 | 12/2002 | Whitman | |
| 6,491,201 B1 | 12/2002 | Whitman | |
| 6,503,257 B2 | 1/2003 | Grant et al. | |
| 6,522,101 B2 | 2/2003 | Malackowski | |

| | | |
|---|---|---|
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 * | 12/2003 | Milliman et al. ......... 227/175.2 |
| 6,681,979 B2 | 1/2004 | Whitman |
| 6,695,199 B2 | 2/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 * | 6/2005 | Swayze et al. ........... 227/176.1 |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,818 B2 * | 2/2006 | Shelton et al. ........... 227/176.1 |
| 7,032,798 B2 | 4/2006 | Whitman et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,098,794 B2 | 8/2006 | Lindsay et al. |
| 7,111,769 B2 | 9/2006 | Wales et al. |
| 7,140,527 B2 | 11/2006 | Ehrenfels et al. |
| 2003/0216778 A1 | 11/2003 | Weadcock |
| 2004/0028502 A1 | 2/2004 | Cummins |
| 2004/0097987 A1 | 5/2004 | Pugsley et al. |
| 2004/0111081 A1 | 6/2004 | Whitman et al. |
| 2004/0122471 A1 | 6/2004 | Toby et al. |
| 2004/0167572 A1 | 8/2004 | Roth et al. |
| 2004/0232197 A1 | 11/2004 | Shelton et al. |
| 2004/0232199 A1 | 11/2004 | Shelton, IV et al. |
| 2004/0243176 A1 | 12/2004 | Hahnen et al. |
| 2005/0006434 A1 | 1/2005 | Wales et al. |
| 2005/0021026 A1 | 1/2005 | Daily |
| 2005/0070958 A1 | 3/2005 | Sayze et al. |
| 2005/0107824 A1 | 5/2005 | Hillstead et al. |
| 2005/0131390 A1 | 6/2005 | Heinrich et al. |
| 2005/0165415 A1 | 7/2005 | Wales |
| 2005/0173490 A1 | 8/2005 | Shelton, IV |
| 2005/0187576 A1 | 8/2005 | Whitman et al. |
| 2005/0203550 A1 | 9/2005 | Laufer et al. |
| 2005/0230453 A1 | 10/2005 | Viola |
| 2006/0011699 A1 | 1/2006 | Olson et al. |
| 2006/0025813 A1 | 2/2006 | Shelton, IV et al. |
| 2006/0025816 A1 | 2/2006 | Shelton, IV |
| 2006/0100643 A1 | 5/2006 | Laufer et al. |
| 2006/0122636 A1 | 6/2006 | Ballly et al. |
| 2006/0142772 A1 | 6/2006 | Ralph et al. |
| 2006/0151567 A1 | 7/2006 | Roy |
| 2006/0190028 A1 | 8/2006 | Wales et al. |

FOREIGN PATENT DOCUMENTS

| | | |
|---|---|---|
| EP | 0122046 | 10/1984 |
| EP | 0552050 | 7/1993 |
| EP | 0552423 | 7/1993 |
| EP | 0639349 | 2/1994 |
| EP | 0630612 | 12/1994 |
| EP | 0634144 | 1/1995 |
| EP | 0656188 | 6/1995 |
| EP | 0679367 | 11/1995 |
| EP | 0685204 | 12/1995 |
| EP | 0699418 | 3/1996 |
| EP | 0705570 | 4/1996 |
| EP | 0705571 | 4/1996 |
| EP | 0667119 | 7/1996 |
| EP | 0760230 | 2/1999 |
| EP | 1086713 | 3/2001 |
| EP | 1256318 | 5/2001 |
| EP | 1238634 | 9/2002 |
| EP | 1426012 | 6/2004 |
| EP | 1479346 | 11/2004 |
| EP | 1520525 | 4/2005 |
| EP | 1550408 | 7/2005 |
| EP | 1064883 | 8/2005 |
| EP | 1621141 | 2/2006 |
| EP | 1045672 | 8/2006 |
| EP | 1617768 | 8/2006 |
| EP | 1129665 | 11/2006 |
| EP | 1256317 | 12/2006 |
| JP | 7051273 | 2/1995 |
| JP | 8033641 | 2/1996 |
| JP | 8229050 | 9/1996 |
| JP | 2001286477 | 10/2001 |
| JP | 2002369820 | 12/2002 |
| JP | 2005103293 | 4/2005 |
| WO | WO 99/15086 | 4/1999 |
| WO | WO 99/34744 | 7/1999 |
| WO | WO 00/72762 | 12/2000 |
| WO | WO 00/72765 | 12/2000 |
| WO | WO 01/05702 | 1/2001 |
| WO | WO 01/62158 | 8/2001 |
| WO | WO 01/62162 | 8/2001 |
| WO | WO 01/62164 | 8/2001 |
| WO | WO 01/91646 | 12/2001 |
| WO | WO 02/30297 | 4/2002 |
| WO | WO 02/043571 | 6/2002 |
| WO | WO 02/053571 | 6/2002 |
| WO | WO 02/67785 | 9/2002 |
| WO | WO 03/090630 | 11/2002 |
| WO | WO 03/000138 | 1/2003 |
| WO | WO 03/001329 | 1/2003 |
| WO | WO 2003/047436 | 6/2003 |
| WO | WO 03/057048 | 7/2003 |
| WO | WO 03/057058 | 7/2003 |
| WO | WO 03/063694 | 8/2003 |
| WO | WO 03/077769 | 9/2003 |
| WO | WO 03/082126 | 10/2003 |
| WO | WO 03/094747 | 11/2003 |
| WO | WO 03/104702 | 12/2003 |
| WO | WO 04/032763 | 4/2004 |
| WO | WO 2004/096057 | 11/2004 |
| WO | WO 2005/027983 | 3/2005 |

* cited by examiner

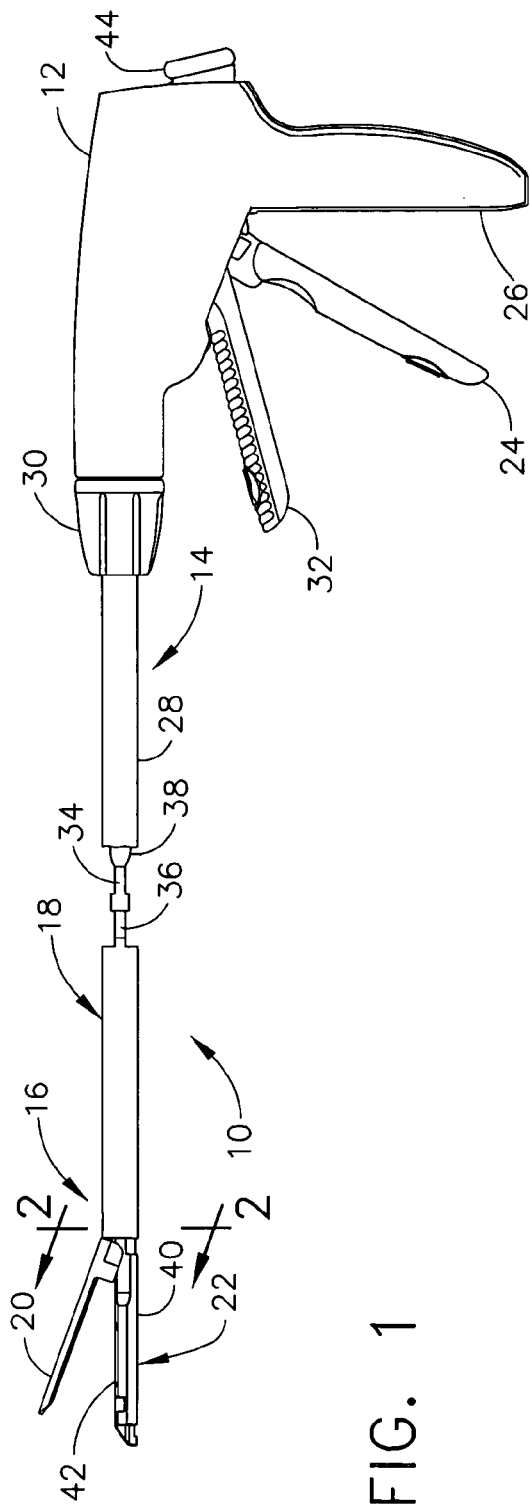
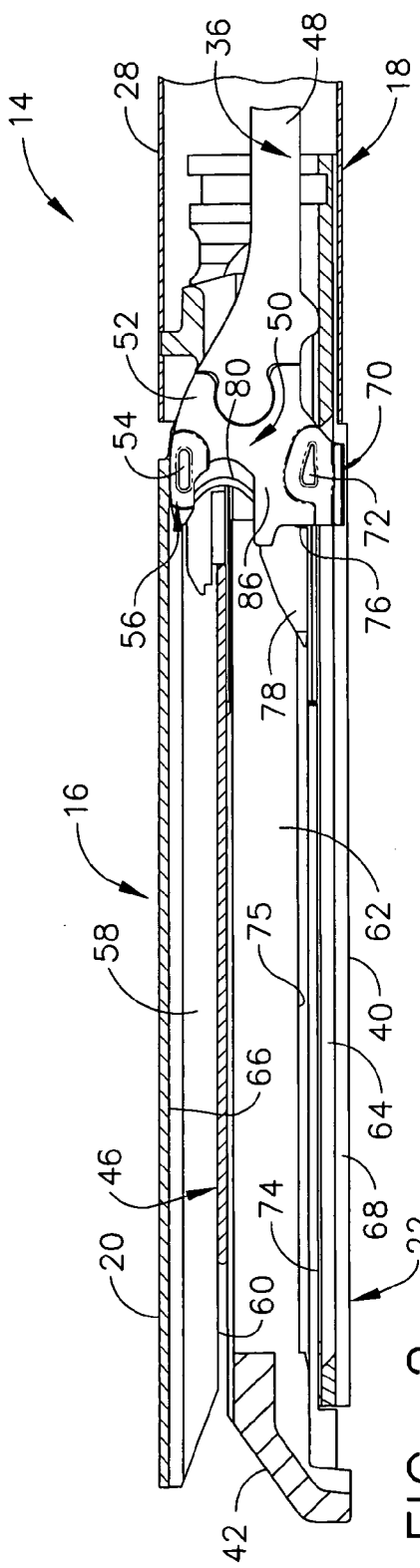
FIG. 1
FIG. 2

SURGICAL STAPLING INSTRUMENT HAVING FORCE CONTROLLED SPACING END EFFECTOR

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments including adding bolstering material to the severed and stapled tissue.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Recently, an improved "E-beam" firing bar was described for a surgical stapling and severing instrument that advantageously included a top pin that slides within an internal slot formed in the upper jaw (anvil) and has a middle pin and bottom foot that slides on opposite sides of a lower jaw of an end effector, or more particularly a staple applying assembly. Distal to the middle pin, a contacting surface actuates a staple cartridge held within an elongate staple channel that forms the lower jaw. Between the contacting surface and the top pin, a cutting surface, or knife, severs tissue clamped between the anvil and the staple cartridge of the lower jaw. Since both jaws are thus engaged by the E-beam, the E-beam maintains a desired spacing between the jaws to ensure proper staple formation. Thus, if a lesser amount of tissue is clamped, the E-beam holds up the anvil to ensure sufficient spacing for the staples to properly form against an undersurface of the anvil. In addition, if a greater amount of tissue is clamped, the E-beam draws down the anvil to ensure that the spacing does not exceed the length of the staple such that ends of each staple are not sufficiently bent to achieve a desired degree of retention. Such an E-beam firing bar is described in U.S. patent application Ser. No. 10/443,617, entitled "Surgical Stapling Instrument Incorporating an E-Beam Firing Mechanism", filed on May 20, 2003, the disclosure of which is hereby incorporated by reference in its entirety.

While an E-beam firing bar has many advantages for a surgical stapling and severing instrument, often it is desirable to sever and staple tissue of various thicknesses. A thin layer of tissue may result in staples that only form loosely, perhaps requiring the need for bolstering material. A thick layer of tissue may result in formed staples that exert a strong compressive force on the captured tissue, perhaps resulting in necrosis, bleeding or poor staple formation/retention. Rather than limiting the range of tissue thicknesses that are appropriate for a given surgical stapling and severing instrument, it would be desirable to accommodate a wider range of tissue thickness with the same surgical stapling and severing instrument.

Consequently, a significant need exists for an improved surgical stapling and severing instrument that incorporates a staple applying assembly (end effector) that adjusts to the amount of tissue that is clamped.

BRIEF SUMMARY OF THE INVENTION

The invention overcomes the above-noted and other deficiencies of the prior art by providing a surgical instrument that incorporates a firing bar that translates through a staple applying assembly having a lower jaw and a pivotally attached upper jaw, engaging each to assist in maintaining the desired spacing between inner surfaces that compress tissue in between. Advantageously, the distance between the two jaws is allowed to flex apart slightly to allow for a larger thickness of compressed tissue, yet the firing bar prevents excessive flexure that would exceed the limits on the device to form staples through the compressed tissue. Thereby, enhanced clinical flexibility is achieved with the same surgical instrument being suitable for a larger range of surgical procedures or to accommodate variations in the patient population.

In one aspect of the invention, a surgical instrument has a lower jaw that includes an elongate staple channel having a longitudinal channel slot formed therein that receives a staple cartridge. Staples in the staple cartridge have a staple length sized for forming a closed staple between a range of tissue thicknesses. A firing bar has a vertical portion passing through a longitudinal anvil slot in an anvil pivotally attached to the elongate staple channel and passes through the longitudinal channel slot formed in the elongate staple channel. An upper lateral surface extending from the vertical portion exerts an inward compressive force on the anvil during firing translation and a lower lateral surface extending from the vertical portion exerts an inward compressive force on the elongate staple channel during firing translation. The firing bar advantageously accommodates the range of effective staple formation by including a resilient portion that varies in height between a staple forming undersurface of an anvil and an upper surface of the staple cartridge.

In another aspect of the invention, a surgical instrument has an anvil that is pivotally coupled to the elongate staple channel and includes an anvil channel that is internally formed. In particular, a vertical slot inwardly opens along a longitudinal axis of the anvil and has left and right rectangular prism-shaped recesses communicating with, bisected by, and transverse to the vertical slot, wherein said left and right rectangular prism-shaped recesses extend substantially along the longitudinal length of the vertical slot. A firing device that includes a distally presented cutting edge for severing tissue is longitudinally received between the elongate staple channel and the vertical slot of the anvil channel of the anvil. An upper member of the firing device has left and right lateral upper pins sized to slidingly engage upper and lower inner surfaces of the left and right rectangular-shaped recesses of the anvil channel. A lower member of the firing device engages the channel slot in the elongate staple cartridge. A middle member of the firing device actuates the staple cartridge by distally translating a wedge member of the staple cartridge. The firing device positively engages both the elongate staple channel and the anvil during longitudinal firing travel to provide spacing in between for staple formation. Engagement of the firing device during firing maintains vertical spacing between the elongate staple channel and the anvil resisting both pinching due to an inadequate clamped tissue and partial opening due to an excessive amount of clamped tissue. This affirmative spacing is advantageously varied within an effective range of the staple length of the staple cartridge by incorporating a resilient portion in the firing device to allow some flexure to accommodate an increased compression load due to a thicker layer of clamped tissue.

In yet another aspect of the invention, the surgical instrument advantageously operates through an elongate shaft with a closed end effector of upper and lower jaws suitably sized for insertion through a cannula of a trocar to an insufflated body cavity or body lumen.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 is a left side view in elevation of a surgical stapling and severing instrument with an open end effector (staple applying assembly) with a shaft partially cut away to expose a firing member of a proximal firing rod and distal firing bar guided by a frame ground and encompassed by a closure sleeve.

FIG. 2 is a left side view of a closed end effector (staple applying assembly) with a retracted force adjusted height firing bar consistent with the present invention of the surgical stapling and severing instrument of FIG. 1 taken in longitudinal vertical cross section along lines 2—2.

DETAILED DESCRIPTION OF THE INVENTION

Figure 3:
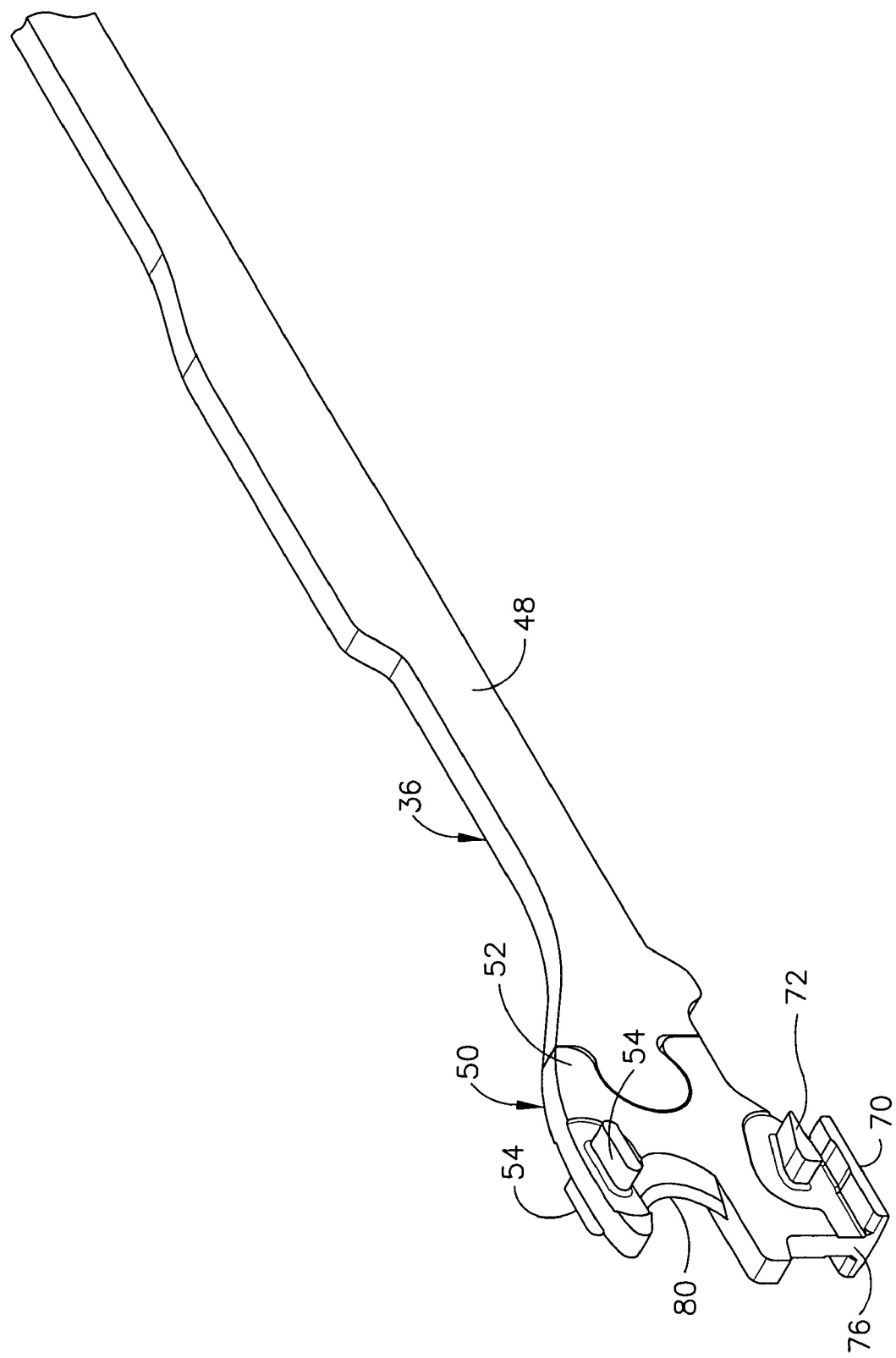
FIG. 3 is a left isometric view of the force adjusted (compliant) height firing bar of FIG. 2.

Turning to the Drawings, wherein like numerals denote like components throughout the several views, in FIG. 1, a surgical stapling and severing instrument 10 includes a handle portion 12 that is manipulated to position an implement portion 14 including a fastening end effector, depicted as a staple applying assembly 16, distally attached to an elongate shaft 18. The implement portion 14 is sized for insertion through a cannula of a trocar (not shown) for an endoscopic or laparoscopic surgical procedure with an upper jaw (anvil) 20 and a lower jaw 22 of the staple applying assembly 16 closed by depression of a closure trigger 24 toward a pistol grip 26 of the handle portion 12, which advances an outer closure sleeve 28 of the elongate shaft 18 to pivot shut the anvil 20.

Once inserted into an insufflated body cavity or lumen, the surgeon may rotate the implement portion 14 about its longitudinal axis by twisting a shaft rotation knob 30 that engages across a distal end of the handle 12 and a proximal end of the elongate shaft 18. Thus positioned, the closure trigger 24 may be released, opening the anvil 20 so that tissue may be grasped and positioned. Once satisfied with the tissue held in the staple applying assembly 16, the surgeon depresses the closure trigger 24 until locked against the pistol grip 26, clamping tissue inside of the staple applying assembly 16.

Then a firing trigger 32 is depressed, drawn toward the closure trigger 24 and pistol grip 26, thereby distally advancing a firing member, depicted as including a proximal firing rod 34 attached to a distal firing bar 36, that is supported within a handle portion 12 to the staple applying assembly 16. The firing bar 36 engages an elongate staple channel 40 and actuates a staple cartridge 42 contained therein, both forming the lower jaw 22. The firing bar 36 also engages the closed anvil 20. After releasing the firing trigger 32 to retract the firing bar 36, depression of a closure release button 44 unclamps the closure trigger 24 so that the closure sleeve 28 may be retracted to pivot and open the anvil 20 to release the severed and stapled tissue from the staple applying assembly 16.

In FIG. 2, the staple applying assembly 16 is closed upon compressed tissue 46. In FIGS. 2-3, the firing bar 36 has a proximal portion 48 that is attached to a distal E-beam 50 that translates within the staple applying assembly 16. As depicted with the firing bar 36 retracted, a vertical portion 52 of the E-beam 50 resides essentially aft of the staple cartridge 42, as after a new staple cartridge 42 has been inserted into the elongate staple channel 40. An upper pin 54 that extends laterally from an upper portion of the vertical portion 52 of the E-beam 50 initially resides within an anvil pocket 56 recessed near a proximal pivoting end of the anvil 20. As the E-beam 50 is distally advanced during firing, the vertical portion 52 passes through a narrow longitudinal anvil slot 58 (FIGS. 1, 11) formed in an undersurface 60 of the anvil 20, a proximally open vertical slot 62 formed in the staple cartridge 42 and an underlying longitudinal channel slot 64 formed in the elongate staple channel 40.

Figure 11:
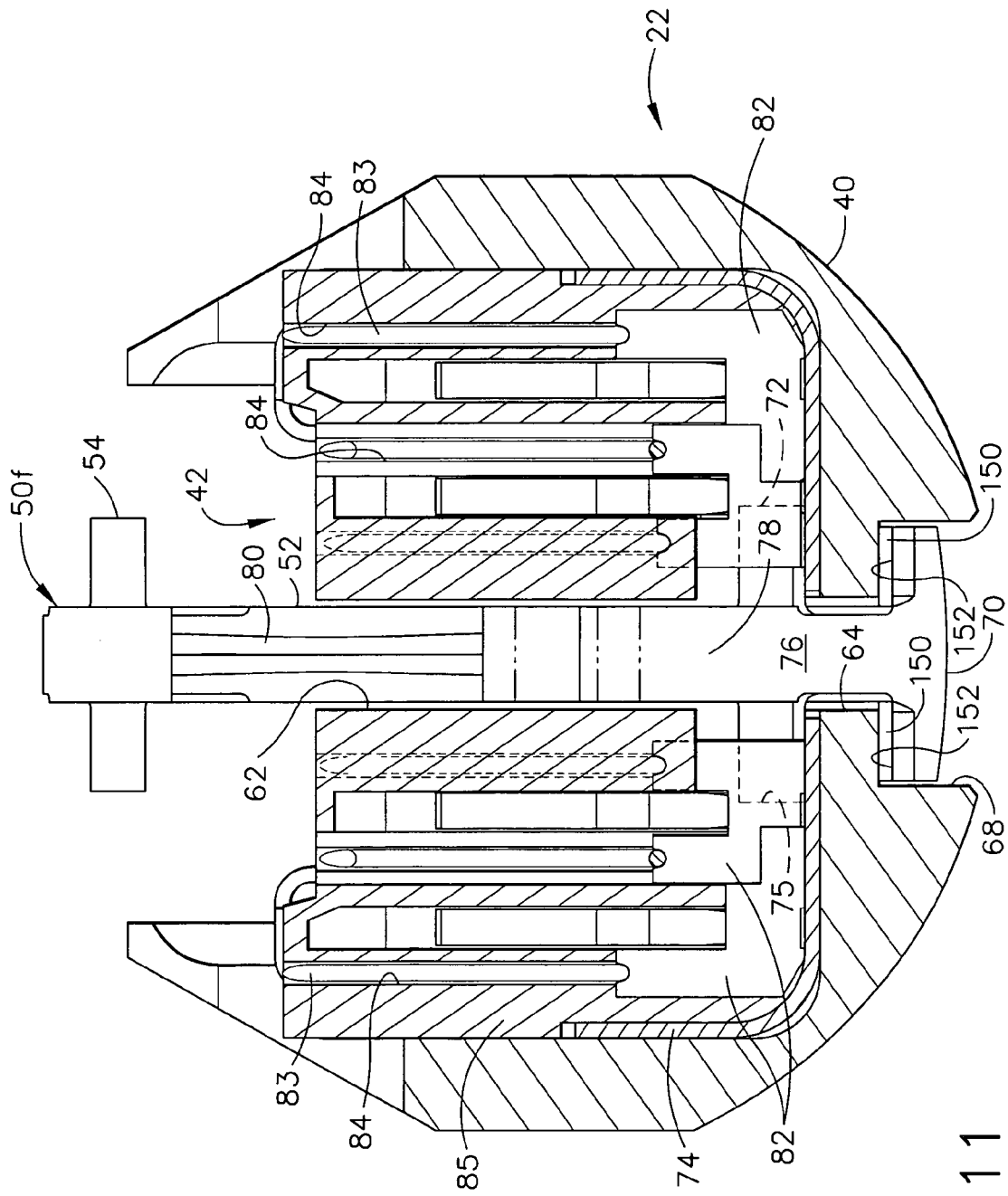
FIG. 11 is a front view in elevation taken in vertical and transverse cross section through the padded lower foot of the end effector (staple applying assembly) of the surgical stapling and severing instrument of FIG. 1.

In FIGS. 2, 11, the narrow longitudinal anvil slot 58 (FIG. 2) communicates upwardly to a laterally widened longitudinal anvil channel 66 sized to slidingly receive the upper pin 54. The longitudinal channel slot 64 communicates downwardly to a laterally widened longitudinal channel track 68 that receives a lower foot 70, which is sized to slide therein and is attached at a bottom of the vertical portion 52 of the E-beam 50. A laterally widened middle pin 72 extending from the vertical portion 52 of the E-beam 50 is positioned to slide along a top surface of a bottom tray 74 of the staple cartridge 42, which in turn rests upon the elongate staple channel 40. A longitudinal firing recess 75 formed in the staple cartridge 42 above the bottom tray 74 is sized to allow the middle pin 72 to translate through the staple cartridge 42.

A distal driving surface 76 of the vertical portion 52 of the E-beam 50 is positioned to translate through the proximally open vertical slot 62 of the staple cartridge 42 and distally drive a wedge sled 78 proximally positioned in the staple cartridge 42. The vertical portion 52 of the E-beam 50 includes a cutting surface 80 along a distal edge above the distal driving surface 76 and below the upper pin 54 that severs the clamped tissue 46 simultaneously with this stapling.

With particular reference to FIG. 11, it should be appreciated that the wedge sled 78 drives upwardly staple drivers 82 that in turn drive upwardly staples 83 out of staple apertures 84 formed in a staple body 85 of the staple cartridge 42 to form against the undersurface 60 of the anvil 20 (FIG. 2).

In FIGS. 2, 11, advantageously, the illustrative spacing, denoted by arrow 86 (FIG. 2), between the upper pin 54 is compliantly biased toward a compressed state wherein 0.015 inches of compressed tissue 46 is contained in the staple applying assembly 16. However, a larger amount of compressed tissue 46 up to about 0.025 inches is allowed by an inherent flexure of the E-beam 50. Excessive flexure, of perhaps up to 0.030 inches, is avoided should the length of staples be insufficient to form with the additional height. It should be appreciated that these dimensions are illustrative for a staple height of 0.036 inches. The same would be true for each category of staple, however.

Figure 4:
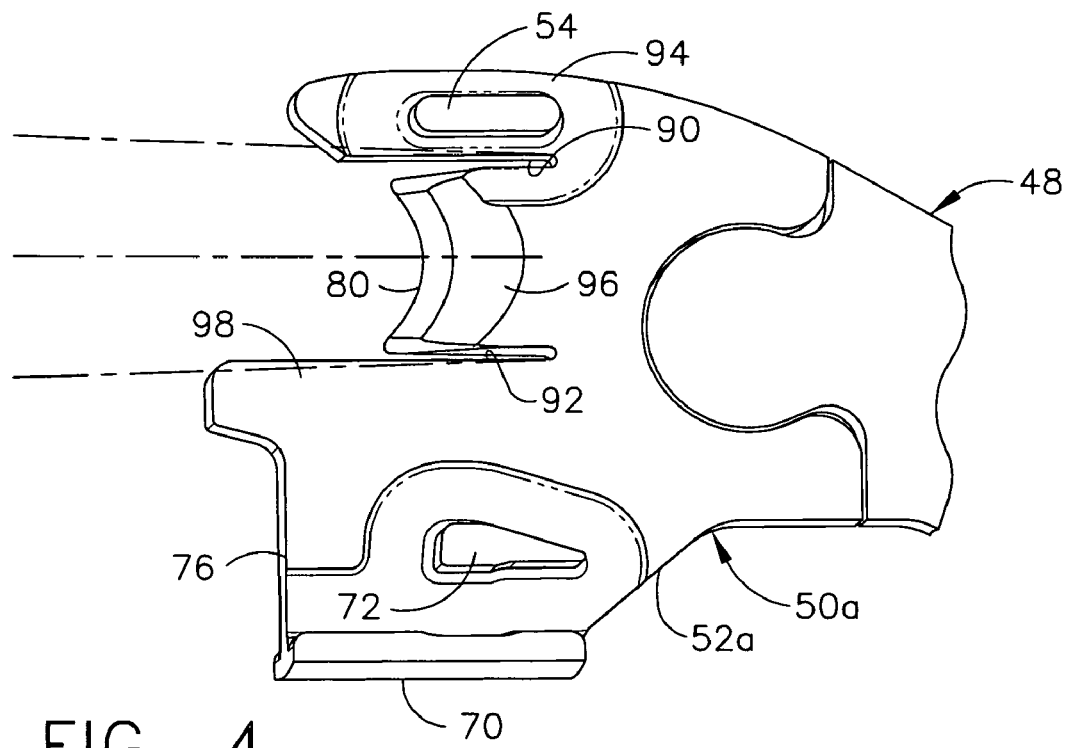
FIG. 4 is a left side view of a distal portion ("E-beam") of a first version of the force adjusted height firing bar of FIG. 2 having horizontal slits formed respectively between the top pin and cutting surface and between the middle pin and the cutting surface to enhance vertical flexure.

In FIG. 4. a first version of a compliant E-beam 50a includes top and bottom horizontal slits 90, 92 from a distal edge of the vertical portion 52a, perhaps formed by electro drilling machine (EDM). The vertical portion 52a thus contains a vertically compliant top distally projecting arm 94 containing the upper pin 54, a knife flange 96 containing the cutting surface 80, and a lower vertical portion 98 containing the distal driving surface 76, middle pin 72 and lower foot 70. The horizontal slits 90, 92 allow a compliant vertical spacing by allowing the top distally arm 94 to pivot upwardly to adjust to increased force from compressed tissue 46 (not shown).

Figure 5:
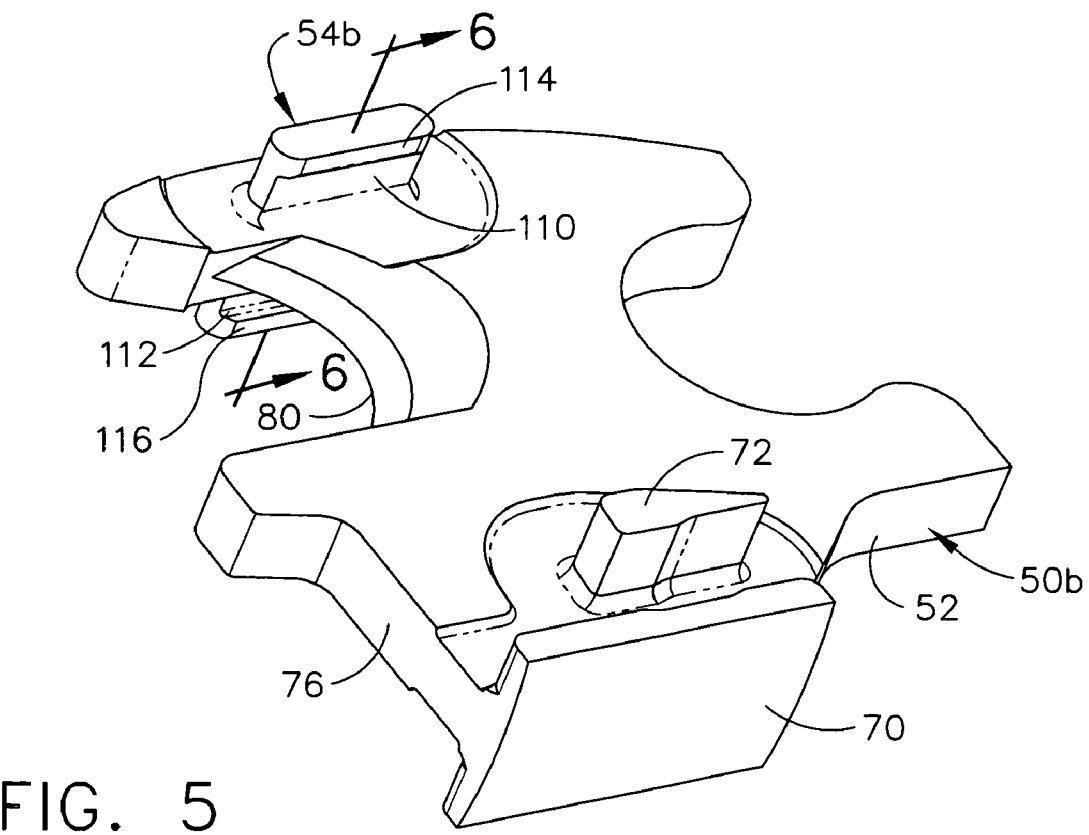
FIG. 5 is a lower left isometric view of a distal portion ("E-beam") of a second version of the force adjusted firing bar of FIG. 2 having a relieved lower area of an upper pin to enhance vertical flexure.
Figure 6:
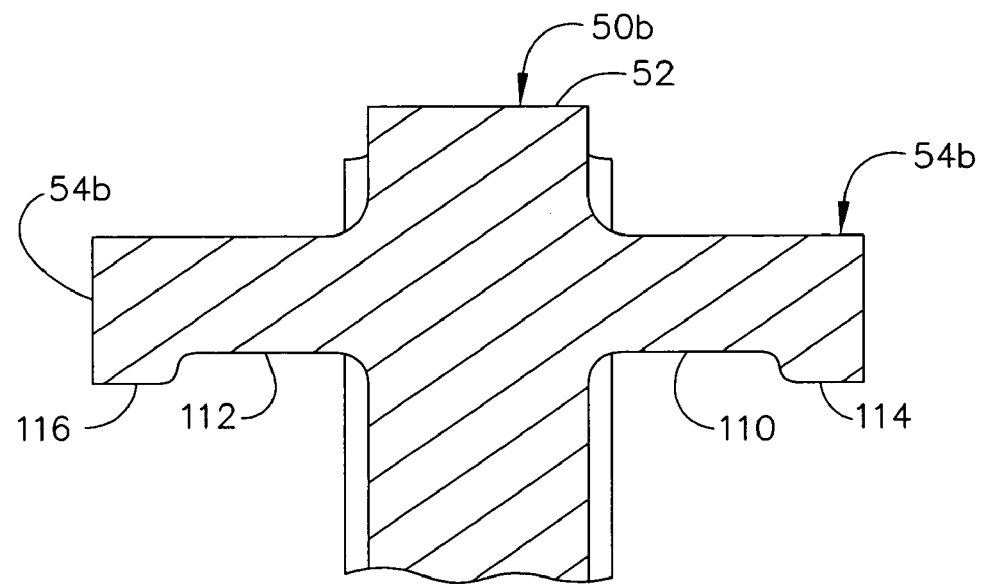
FIG. 6 is a front view in elevation of an upper portion of the E-beam of FIG. 5 taken in vertical and transverse cross section through the upper pin along lines 6—6.

In FIGS. 5–6, a second version of a compliant E-beam 50b includes left and right lower relieved areas 110, 112 formed into an upper pin 54b to each side of the vertical portion 52, leaving left and right lower bearing points 114, 116 respectively. The outboard position of the bearing points 114, 116 provides a long moment arm to exert the force to flex. It should be appreciated given the benefit of the present disclosure that the dimensions of the relieved areas 110, 112 and the choice of materials for the compliant E-beam 50b may be selected for a desired degree of flexure, given the staple size and other considerations.

Figure 7:
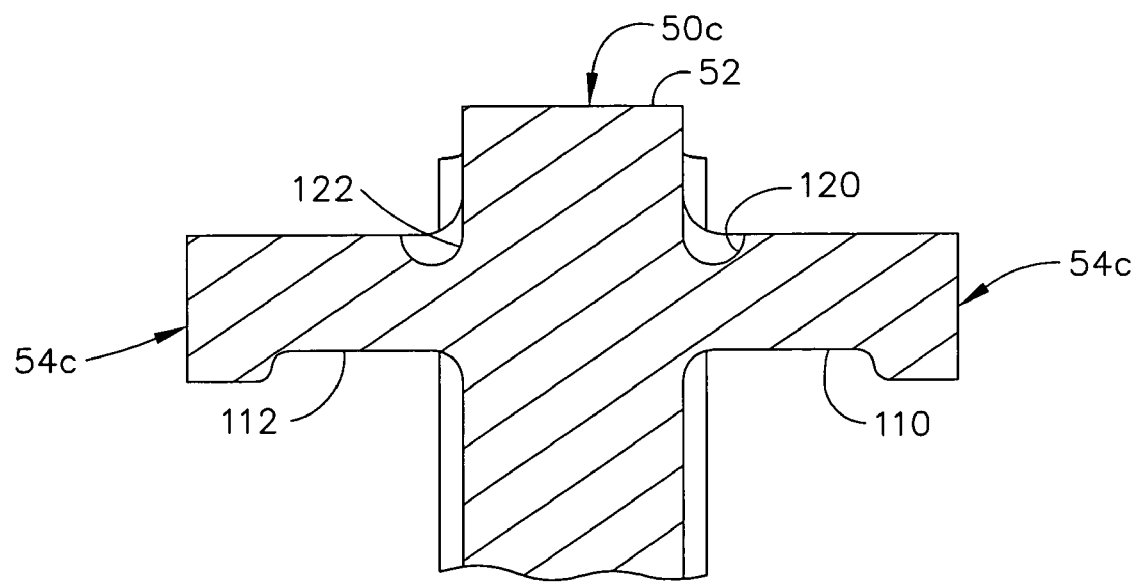
FIG. 7 is a front view of an upper portion of a third version of the E-beam of FIG. 5 taken in vertical and transverse cross section along lines 6—6 but further including relieved upper root attachments of the top pin for enhanced vertical flexure.

In FIG. 7, a third version of a compliant E-beam 50c is as described above in FIGS. 5–6 with further flexure provided by left and right upper narrow relieved areas 120, 122 formed into opposite top root surfaces of an upper pin 54c proximate to the vertical portion 52.

Figure 8:
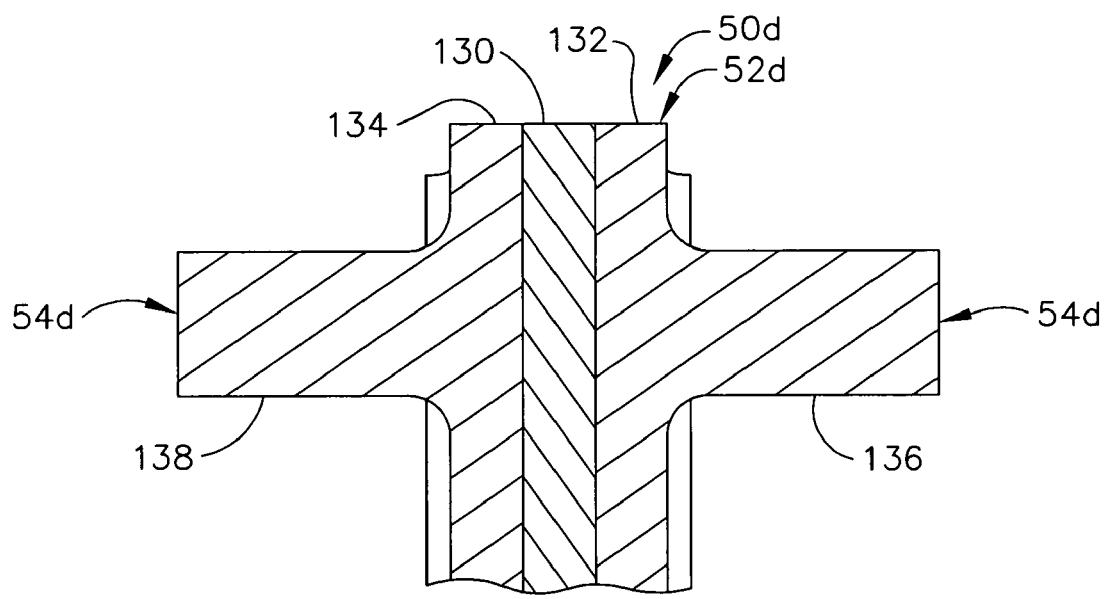
FIG. 8 is a front view of an upper portion of a fourth version of the E-beam of FIG. 5 taken in vertical and transverse cross section along lines 6—6 but including a resilient inner vertical laminate layer instead of a relieved undersurface of the top pin for enhanced vertical flexure.

In FIG. 8, a fourth version of a compliant E-beam 50d is as described for FIGS. 2–3 with an added feature of a composite/laminate vertical portion 52d that includes a central resilient vertical layer 130 sandwiched between left and right vertical layers 132, 134 that support respectively left and right portions 136, 138 of an upper pin 54d. As the left and right portions 136, 138 are flexed either up or down, the resulting bowing of the left and right vertical layers 132, 134 are accommodated by a corresponding compression or expansion of the central resilient vertical layer 130.

Figure 9:
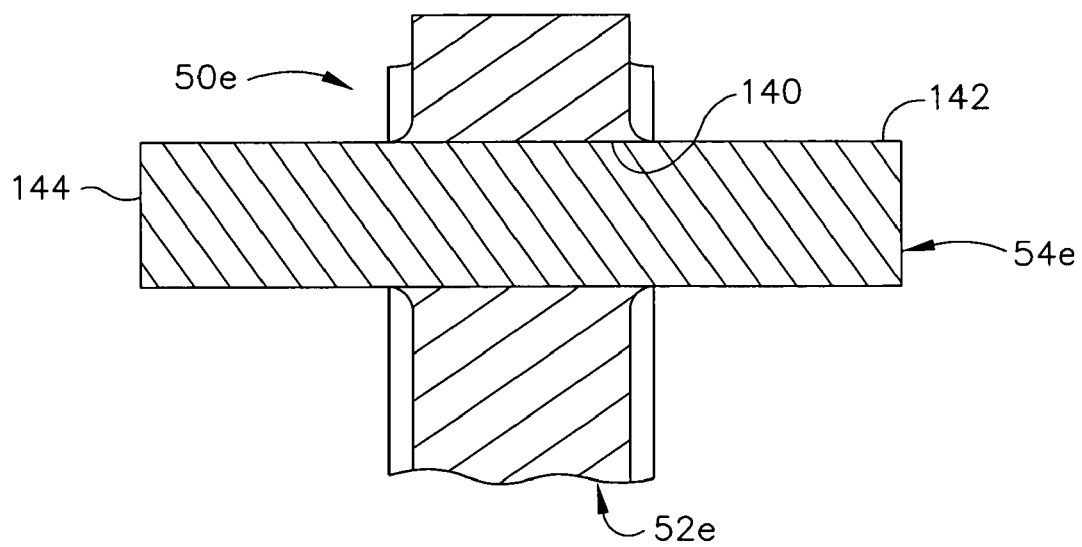
FIG. 9 is a front view of an upper portion of a fifth version of the E-beam of FIG. 5 taken in vertical and transverse cross section along lines 6—6 but including an upper pin formed of a resilient material instead of a relieved undersurface of the upper pin for enhanced vertical flexure.

In FIG. 9, a fifth version of a compliant E-beam 50e is as described for FIGS. 2–3 with an added feature of a discrete upper pin 54e formed of a more flexible material that is inserted through a horizontal aperture 140 through a vertical portion 52e. Thus, left and right outer ends 142, 144 of the discrete upper pin 54e flex in accordance with loading forces.

Figure 10:
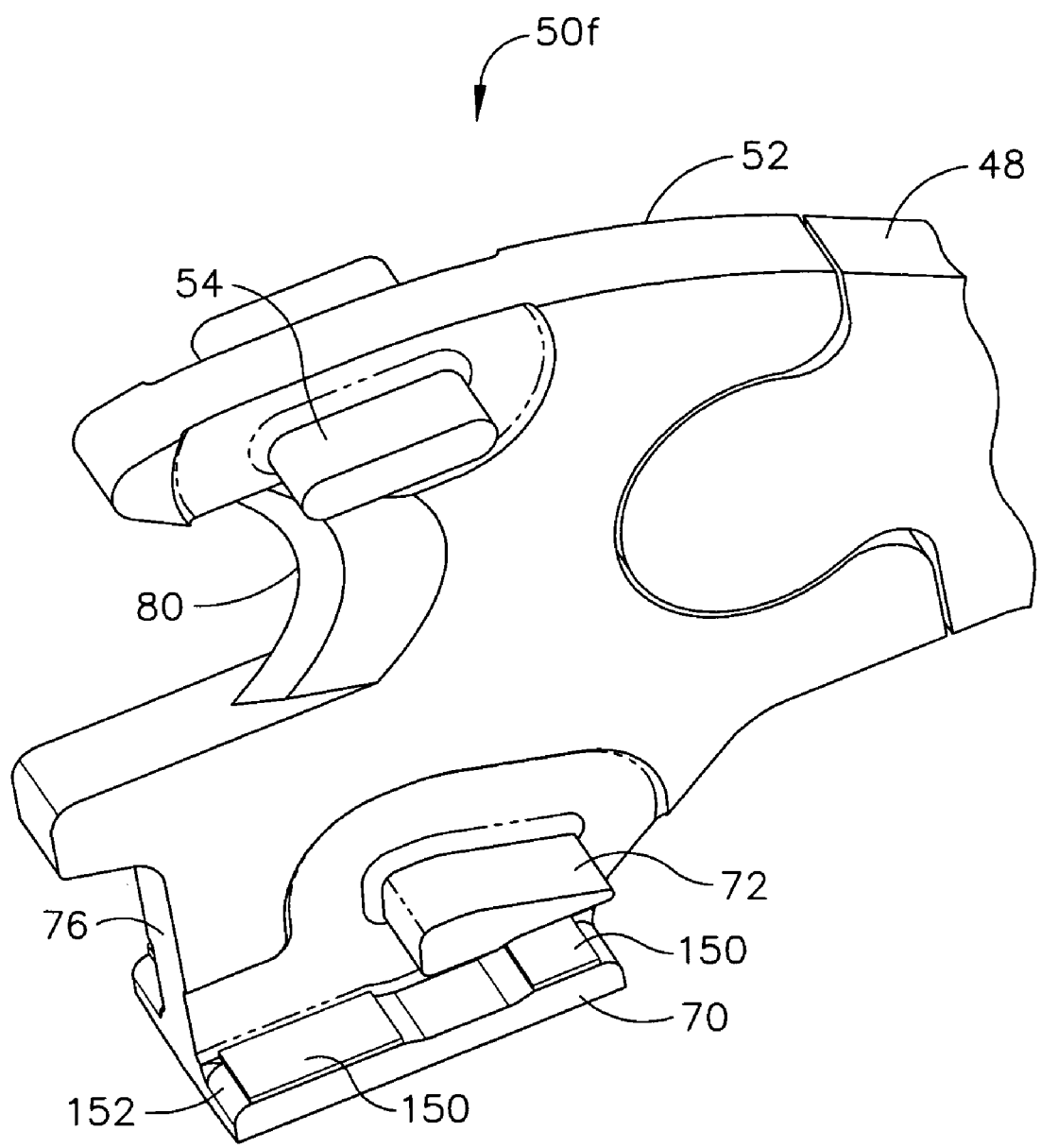
FIG. 10 is an upper left isometric view of a distal portion ("E-beam") of a sixth version of the force adjusted firing bar of FIG. 2 having resilient material upon a bottom foot to enhance vertical flexure.

Alternatively or in addition to incorporating flexure into an upper pin 54, in FIGS. 10–11, a sixth version of a compliant E-beam 50f as described for FIGS. 2–3 further includes resilient pads 150 that are attached to upper surfaces 152 of the bottom foot 70. The resilient pads 150 adjust the spacing of the upper pin 54 in accordance to the compression force experienced at the bottom foot 70.

Figure 12:
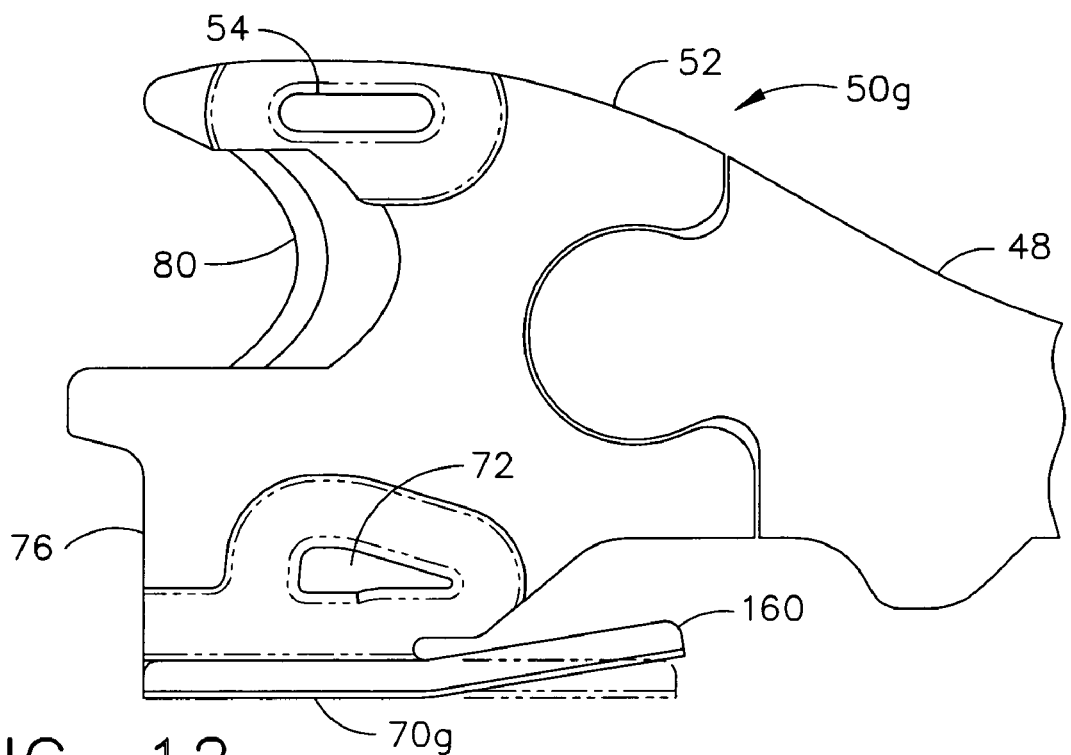
FIG. 12 is a left view in elevation of a distal portion ("E-beam") of a seventh version of the force adjusted firing bar of FIG. 2 having a proximally and upwardly extended spring arm attached to a lower foot to enhance vertical flexure.

In FIG. 12, a seventh version of a compliant E-beam 50g is as described above for FIGS. 2–3 with the added feature of a bottom foot (shoe) 70g having an upwardly aft extended spring finger 160 that resiliently urges the E-beam 50g downwardly to adjust vertical spacing in accordance with loading force.

Figure 13:
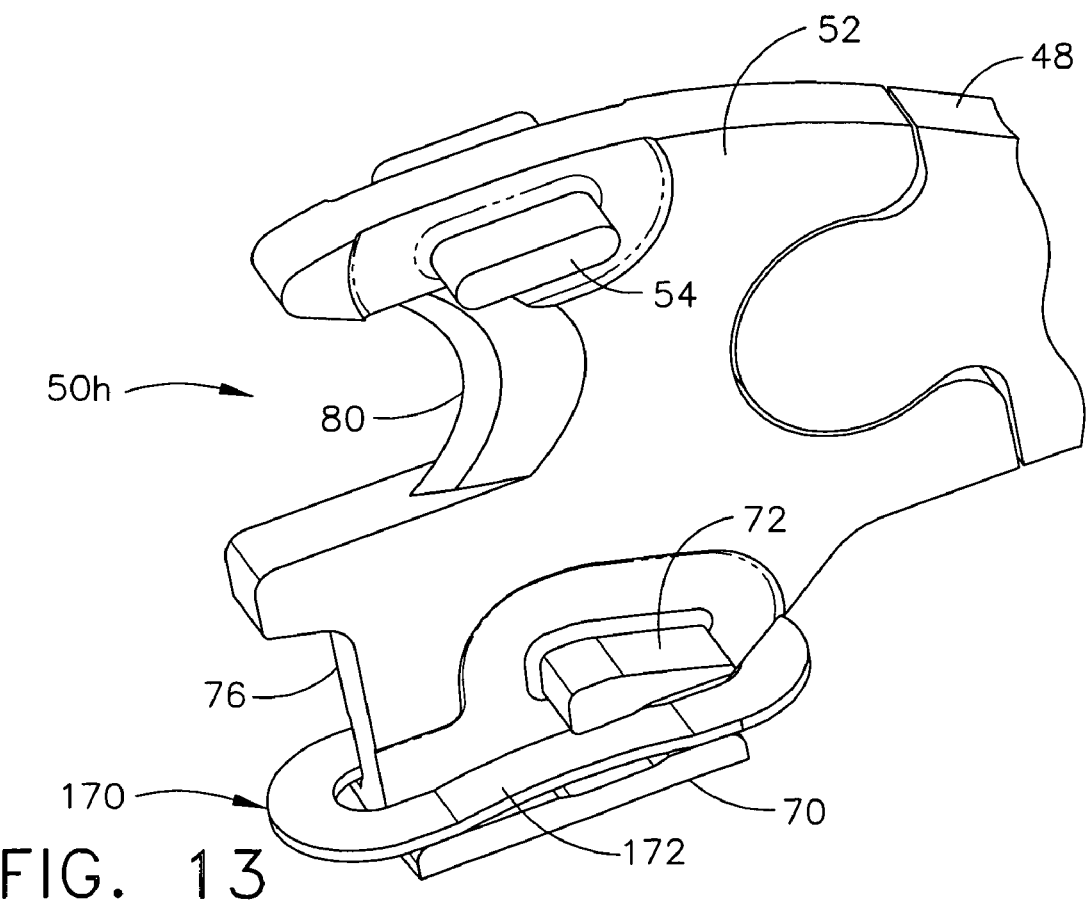
FIG. 13 is a left top isometric view of a distal portion ("E-beam") of an eighth version of the force adjusted firing bar of FIG. 2 having a spring washer encompassing a lower foot to enhance vertical flexure.

In FIG. 13, an eighth version of a compliant E-beam 50h is as described above in FIGS. 2–3 with the added feature of an oval spring washer 170 resting upon the bottom foot 70 encircling the vertical portion 52 and having an upwardly bowed central portion 172 that resiliently urges the E-beam 50h downwardly to adjust vertical spacing in accordance with loading force.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a manually operated surgical stapling and severing instrument 10 is depicted for clarity, it should be appreciated that robotically manipulated and/or controlled fastening devices may incorporate a force controlled firing bar.

For another example, a compliant E-beam consistent with aspects of the present invention may include engagement to an anvil similar to the engagement in the illustrative versions of two structures that slide against opposite sides of the elongate staple channel. Similarly, a compliant E-beam may engage a lower jaw by having a laterally widened portion that slides internally within a channel formed in a lower jaw structure.

As yet an additional example, in the illustrative version, the staple cartridge 42 is replaceable so that the other portions of the staple applying assembly 16 may be reused. It should be appreciated given the benefit of the present disclosure that applications consistent with the present invention may include a larger disposable portion, such as a distal portion of an elongate shaft and the upper and lower jaws with a staple cartridge permanently engaged as part of the lower jaw.

As yet another example, the illustrative E-beam advantageously affirmatively spaces the upper and lower jaws from each other. Thus, the E-beam has inwardly engaging surfaces that pull the jaws together during firing in instances where a larger amount of compressed tissue tends to spread the jaws. Thereby the E-beam prevents malformation of staples due to exceeding their effective length. In addition, the E-beam has outwardly engaging surfaces that push the jaws apart during firing in stances where a small amount of tissue or other structure attributes of the instrument tend to pinch the jaws together that may result in staple malformation. Either or both functions may be enhanced by applications consistent with aspects of the invention wherein inherent flexure in the E-beam adjusts to force to allow a degree of closing of the jaws or of opening of the jaws.

What is claimed is:

1. A surgical instrument, comprising:
  a handle portion operable to produce a firing motion;
  an implement portion responsive to the firing motions from the handle portion, the implement portion comprising:
    an elongate staple channel coupled to the handle portion and including a channel slot,
    a staple cartridge having an upper surface and received in the elongate staple channel and containing a plurality of staples each having a staple length sized for forming a closed staple between a first height and a second height,
    a wedge member movably positioned in the implement portion to drive the plurality of staples of the staple cartridge;
    an anvil pivotally coupled to the elongate staple channel and including an anvil channel comprising a vertical slot inwardly open along a longitudinal axis of the anvil and comprising left and right rectangular prism-shaped recesses communicating with, bisected by, and transverse to the vertical slot, wherein said left and right rectangular prism-shaped recesses extend substantially along the longitudinal length of the vertical slot;
    a firing device including a distally presented cutting edge longitudinally received between the elongate staple channel and the vertical slot of the anvil channel of the anvil, an upper member comprised of left and right lateral upper pins sized to slidingly engage upper and lower inner surfaces of the left and right rectangular-shaped recesses of the anvil channel, a lower member engaging the channel slot, and a middle member operable to actuate the staple cartridge by distally translating the wedge member through the staple cartridge, the firing device positively engaging both the elongate staple channel and the anvil during longitudinal firing travel to provide spacing therebetween for staple formation, and wherein engagement of the firing device during firing maintains vertical spacing between the elongate staple channel and the anvil resisting both pinching due to an inadequate clamped tissue and partial opening due to an excessive amount of clamped tissue; and
    a resilient portion of the firing device allowing a height between the staple forming undersurface of the anvil and the upper surface of the staple cartridge to vary between the first and second heights of the closed staples in relation to the clamped tissue thickness.

2. The surgical instrument of claim 1, wherein the anvil forms an inwardly biased relation to the elongate staple channel configured to assist the firing device in affirmatively spacing between the anvil and elongate staple channel during actuation of the staple cartridge.

3. The surgical instrument of claim 2, further comprising a closure member operatively configured to longitudinally transfer the closure motion to the implement portion to inwardly bias distal ends of the anvil and the elongate staple channel to assist the firing device in affirmatively spacing the anvil and elongate staple channel during actuation of the staple cartridge.

4. The surgical instrument of claim 1, wherein the staple cartridge is a selected type of a plurality of staple cartridge types, each staple cartridge type characterized by a thickness selected for a desired spacing between the anvil and elongate staple channel and characterized by staples having a length suitable for the desired spacing.

5. The surgical instrument of claim 4, wherein the wedge member comprises a wedge sled having a plurality of connected camming wedges each having a preselected height configured for the selected type of staple cartridge, the middle member of the firing device oriented to abut each of the plurality of staple cartridge types.

6. A surgical instrument comprising:
  a handle portion operable to produce a firing motion and a closing motion; and
  an implement portion responsive to the firing motions from the handle portion and diametrically dimensioned for endo-surgical use, the implement portion comprising:
    a shaft coupled to the handle portion operable to separately transfer the firing motion and the closing motion,
    an elongate staple channel coupled to the shaft and including a channel slot and operatively configured to receive a staple cartridge having an upper surface,
    an anvil pivotally coupled to the elongate staple channel, responsive to the closing motion from the shaft, and including an anvil channel, and
    a firing device including a distally presented cutting edge longitudinally received between the elongate staple channel and the anvil, the firing device configured to affirmatively space the anvil from the elongate staple channel during longitudinal travel between the anvil and elongate staple channel, a resilient portion of the firing device allowing a height between a staple forming undersurface of the anvil and the upper surface of the staple cartridge to vary between the first and second heights in relation to the clamped tissue thickness, wherein the firing device is configured to affirmatively space the anvil from the elongate staple channel during longitudinal travel between the anvil and elongate staple channel by including an upper member having an upper surface and a lower surface that longitudinally slidingly engage the anvil.

7. The surgical instrument of claim 6, wherein the anvil includes a longitudinal slot having an upper surface and a lower surface that slidingly abut respectively the lower surface and upper surface of the upper member of the firing device.

8. The surgical instrument of claim 7, wherein the longitudinal slot comprises an internal longitudinal channel communicating with a narrowed vertical slot, and wherein the firing device translates in the narrowed vertical slot and includes an upper member having the upper and lower surfaces that reside within the internal longitudinal channel for affirmatively spacing the anvil from the elongate staple channel.

9. The surgical instrument of claim 6, wherein the firing device is configured to affirmatively space the anvil from the elongate staple channel during longitudinal travel between the anvil and elongate staple channel by including a lower portion having an upper surface and a lower surface that slidingly engage the elongate staple channel.

10. The surgical instrument of claim 9 wherein the lower portion of the firing device comprises a lower pin having the upper surface abutting the elongate staple channel and comprises a middle pin having the lower surface opposingly abutting the elongate staple channel.

11. The surgical instrument of claim 10, wherein the firing device further comprises an upper member having an upper surface and a lower surface that longitudinally slidingly engage the anvil.

12. The surgical instrument of claim 11, wherein the anvil includes an internal longitudinal slot having a narrowed vertical slot, and wherein the firing device translates in the narrowed vertical slot and includes an upper member having upper and lower surfaces that reside within the internal longitudinal slot for affirmatively spacing the anvil from the elongate staple channel.

13. The surgical instrument of claim 6, further comprising a staple cartridge engaged by the elongate staple channel and including a proximally opened slot for receiving the cutting edge of the firing device, the staple cartridge including a plurality of staples cammed upwardly by the distal longitudinal movement of the firing mechanism.

14. The surgical instrument of claim 13, wherein the staple cartridge further includes a plurality of drivers supporting the plurality of staples and a wedge sled responsive to the distal longitudinal movement of the firing mechanism to cam upwardly the drivers and thus form the plurality of staples against the anvil.

15. The surgical instrument of claim 13, wherein the anvil forms an inwardly biased relation to the elongate staple channel configured to assist the firing device in affirmatively spacing between the anvil and elongate staple channel during actuation of the staple cartridge.

16. The surgical instrument of claim 13, wherein the staple cartridge is a selected type of a plurality of staple cartridge types, each staple cartridge type characterized by a thickness selected for a desired spacing between the anvil and elongate staple channel and characterized by staples having a length suitable for the desired spacing.

17. The surgical instrument of claim 16, wherein the wedge sled comprises a plurality of connected camming wedges each having a preselected height configured for the selected type of staple cartridge, the middle member of the firing device oriented to abut each of the plurality of staple cartridge types.

* * * * *